United States Patent
Burakowska-Meise et al.

(10) Patent No.: US 10,195,577 B2
(45) Date of Patent: *Feb. 5, 2019

(54) PROCESS FOR PRODUCING MICROCAPSULES

(71) Applicant: BASF SE, Ludwigshafen (DE)

(72) Inventors: Ewelina Burakowska-Meise, Reichenbach (DE); Wolfgang Denuell, Mannheim (DE); Ulrich Issberner, Düsseldorf (DE)

(73) Assignee: BASF SE, Ludwigshafen (DE)

(*) Notice: Subject to any disclaimer, the term of this patent is extended or adjusted under 35 U.S.C. 154(b) by 0 days.

This patent is subject to a terminal disclaimer.

(21) Appl. No.: 15/305,682

(22) PCT Filed: Apr. 27, 2015

(86) PCT No.: PCT/EP2015/059004
§ 371 (c)(1),
(2) Date: Oct. 21, 2016

(87) PCT Pub. No.: WO2015/165836
PCT Pub. Date: Nov. 5, 2015

(65) Prior Publication Data
US 2017/0043312 A1 Feb. 16, 2017

(30) Foreign Application Priority Data
Apr. 29, 2014 (EP) .................... 14166360

(51) Int. Cl.
| C11D 3/37 | (2006.01) |
| A61K 8/11 | (2006.01) |
| B01J 13/16 | (2006.01) |
| A61Q 19/00 | (2006.01) |
| B01J 13/14 | (2006.01) |
| A01N 25/28 | (2006.01) |
| A01N 37/22 | (2006.01) |
| A01N 43/10 | (2006.01) |
| A01N 43/56 | (2006.01) |
| A01N 43/90 | (2006.01) |
| B01J 13/18 | (2006.01) |
| A61K 9/50 | (2006.01) |
| C11D 17/00 | (2006.01) |

(52) U.S. Cl.
CPC .............. *B01J 13/14* (2013.01); *A01N 25/28* (2013.01); *A01N 37/22* (2013.01); *A01N 43/10* (2013.01); *A01N 43/56* (2013.01); *A01N 43/90* (2013.01); *A61K 8/11* (2013.01); *A61K 9/5026* (2013.01); *A61K 9/5089* (2013.01); *A61Q 19/00* (2013.01); *B01J 13/16* (2013.01); *B01J 13/18* (2013.01); *C11D 3/3753* (2013.01); *C11D 17/0039* (2013.01)

(58) Field of Classification Search
None
See application file for complete search history.

(56) References Cited

U.S. PATENT DOCUMENTS

| 5,324,584 A * | 6/1994 | Juang ................ B01J 13/16 264/4.1 |
| 5,342,556 A | 8/1994 | Traubel et al. |
| 2005/0221991 A1 | 10/2005 | Wolf et al. |
| 2010/0068525 A1 | 3/2010 | Jung et al. |

FOREIGN PATENT DOCUMENTS

| EP | 0 537 467 A1 | 4/1993 |
| EP | 2 399 667 A1 | 12/2011 |
| EP | 2426172 A1 | 3/2012 |
| EP | 2648211 A1 | 10/2013 |
| JP | H10139818 A | 5/1998 |
| WO | WO-2007/096592 A1 | 8/2007 |
| WO | WO-2011/161229 A1 | 12/2011 |
| WO | WO-2012/107323 A1 | 8/2012 |

OTHER PUBLICATIONS

An English Translation of JP H10-139818A which is provided by JPO (last visit Nov. 20, 2017). (Year: 1998).*
International Search Report in International Patent Application No. PCT/EP2015/059004, dated Jun. 1, 2015.

* cited by examiner

Primary Examiner — Ernst V Arnold
Assistant Examiner — Kyung S Chang
(74) Attorney, Agent, or Firm — Marshall, Gerstein & Borun LLP

(57) ABSTRACT

A process for producing microcapsules containing a shell and a core of a liquid water-insoluble material is disclosed. The microcapsules are prepared using a bifunctional isocyanate, an anionically modified diisocyanate, a bifunctional amine, and a protective colloid. The protective colloid is a polyvinyl alcohol copolymer having hydrolysis degrees from 85 to 99.9%.

10 Claims, No Drawings

PROCESS FOR PRODUCING MICROCAPSULES

CROSS-REFERENCE TO REALTED APPLICATIONS

This is the U.S. national phase of International Application No. PCT/EP2015/059004, filed Apr. 27, 2015, which claims the benefit of European Patent Application No. 14166360.9, filed Apr. 29,2014.

The application relates to a process for producing microcapsules.

Microcapsules are spherical objects which consist of a core and a wall material surrounding the core, wherein the core is a solid, liquid or gaseous substance which is surrounded by the solid (generally polymeric) wall material. They may be solid, i.e. consist of a single material. Microcapsules have a diameter from 1 to 1000 µm, on average.

A multitude of shell materials is known for producing the wall of microcapsules. The shell can consist either of natural, semisynthetic or synthetic materials. Natural shell materials are, for example, gum arabic, agar agar, agarose, maltodextrins, alginic acid or its salts, e.g. sodium alginate or calcium alginate, fats and fatty acids, cetyl alcohol, collagen, chitosan, lecithins, gelatin, albumin, shellac, polysaccharides, such as starch or dextran, polypeptides, protein hydrolyzates, sucrose and waxes. Semisynthetic shell materials are inter alia chemically modified celluloses, in particular cellulose esters and cellulose ethers, e.g. cellulose acetate, ethyl cellulose, hydroxypropylcellulose, hydroxypropylmethylcellulose and carboxymethylcellulose, and also starch derivatives, in particular starch ethers and starch esters. Synthetic shell materials are, for example, polymers such as polyacrylates, polyamides, polyvinyl alcohol or polyurea.

Depending on the type of shell material and the production process, microcapsules are formed in each case with different properties, such as diameter, size distribution and physical and/or chemical properties.

Polyurea core-shell microcapsules obtained by reaction of two diisocyanates and a polyamine are well known in the art for example from WO 2011/161229 or EP-A1-2399667. According to WO 2011/161229 the polyurea microcapsules are prepared in presence of polyvinylpyrrolidone (PVP) as a protective colloid.

WO 2012/107323 discloses polyurea microcapsules having a polyurea shell comprising the reaction product of a polyisocyanate with guanazole and an amino acid in presence of anionic stabilizers or surfactants like anionic polyvinyl alcohol, such as Kuraray Poval 6-77 KL sold by Kuraray.

EP-B-0 537 467 describes microcapsules prepared from isocyanates, which are containing polyethylenoxide groups, in presence of stabilizers like partly saponified polyvinyl acetate or polyvinyl alcohol.

According to WO 2007/096592 microencapsulation can take place in an oil phase which is emulsified into a continuous aqueous phase, generally stabilized by a surfactant system like polyvinyl alcohols, including the carboxylated and sulphonated thereof.

To provide microcapsules with tailored properties novel production processes need to be developed. Especially microcapsules produced to encapsulate water-insoluble ingredients like oils need to have an optimized, enhanced stability against leaking-out of the oil from the capsules into the external phase, particularly in surfactant-based formulations. Moreover, an aqueous dispersion of the microcapsules needs to be stable against separation over a long period of time.

According to the first aspect of the present invention there is provided a process for producing microcapsules which contain a shell and a core of a liquid water-insoluble material, where
(a) a premix (I) is prepared from water and a protective colloid;
(b) a further premix (II) is prepared from a water-insoluble liquid component and at least bifunctional isocyanate (A) or a mixture of two or more different isocyanates containing (A)
(c) the two premixes (I) and (II) are mixed together until an emulsion is formed and
(d) at least a bifunctional amine is then poured into the emulsion from step (c) and
(e) the emulsion is then heated up to at least 50° C. until the microcapsules are formed,
characterized in that the protective colloid is a polyvinyl alcohol copolymer having hydrolysis degrees from 85 to 99.9%.

According to the invention microcapsules with determined sizes and/or size distribution can be produced in a targeted manner. Moreover, it is possible to produce relatively small microcapsules with diameters from 5 to 30 µm. Advantageously, capsules with greater enhanced leakage stability against leakage in surfactant-based formulations are obtained, which show a better performance against separation over a long period of time.

According to the invention a mixture of bifunctional isocayanates (A) and isocyanates (B) can be added in one step or can be added separately from each other.

According to one embodiment of the invention the bifunctional isocyanates (A) are dissolved alone or in a mixture with a further isocyanate (B) in the water-insoluble liquid (also termed "water-insoluble material") which later forms the core of the microcapsules; the premixes (I) and (II) are mixed together until an emulsion is formed and then the amine components are added and the mixture is heated until the capsules are formed.

According to a second embodiment of the invention the bifunctional isocyanates (A) are dissolved alone in the water-insoluble liquid which later forms the core of the microcapsules; the premixes (I) and (II) are mixed together until an emulsion is formed and then the further isocyanate (B) is added before the amine components are added and the mixture is heated until the capsules are formed.

The temperature for the reaction of the isocyanates with the amine components must be at least 50° C., better 60° C., preferably 75 to 90° C. and in particular 85 to 90° C., in order to ensure sufficiently rapid reaction progress.

Here, it may be preferred to increase the temperature in stages (e.g. in each case by 10° C.) until then, following completion of the reaction, the dispersion is cooled down to room temperature (21° C.).

The reaction time typically depends on the batch size and temperature used. Usually, microcapsule formation is established between ca. 60 minutes to 6 h or up to 8 h at the temperatures defined above.

According to the present teaching, the addition of the amine also preferably takes place with the input of energy, e.g. by using a stirring apparatus.

In order to form an emulsion in the present process, the respective mixtures are usually emulsified by processes known to the person skilled in the art, e.g. by introducing energy into the mixture through stirring using a suitable stirrer until the mixture emulsifies. The pH is preferably adjusted using aqueous bases, preference being given to using sodium hydroxide solution (e.g. 5% strength by weight). It may be advantageous to adjust the pH of premix (I) from 3 to 12, preferably between 4 to 10, and in particular in the range from 5 to 10.

Microcapsules

Within the context of the present teaching, the microcapsules have a shell made by a polyaddition between at least bifunctional isocyanates with amines, preferably with polyamines, which leads to polyurea derivatives.

The microcapsules are present in the form of aqueous dispersions, the weight fraction of these dispersions in the microcapsules being favored between 5 and 50% by weight, in particular between 15 to 40% per weight and preferably 20 to 40% by weight. The microcapsules have an average diameter in the range from 1 to 500 µm and preferably from 3 to 50 µm or from 5 to 30 µm.

The particle size determinations specified may be carried out by means of static laser diffraction. The α 50 and 90 values may be based on the volume distribution of the particles.

The microcapsules contain the liquid water-insoluble material, e.g. an oil. The fraction of this oil can vary in the range from 10 to 95% by weight, based on the weight of the microcapsules, where fractions from 70 to 90% by weight may be advantageous. Result of the process are microcapsules—with preferred typical core/shell ratios (w/w) from 20:1 to 1:10, preferably from 5:1 to 2:1 and in particular from 4:1 to 3:1.

The microcapsules which are produced by the present processes are preferably free from formaldehyde.

Protective Colloid

It is state of the art to use protective colloids like polyvinyl alcohols during the microencapsule formation process.

Polyvinyl alcohol (=PVA) corresponds typically in general according to formula

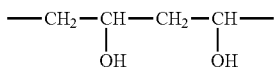

with low amounts (up to 2%) of the formula structure

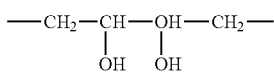

In order to get the benefits of the invention it is essential to use special protective colloids of polyvinyl alcohol. It was found that the obtained microcapsules have superior properties when polyvinyl alcohol copolymers having a hydrolysis degree from 85 to 99.9% are used.

According to the invention the term "polyvinyl alcohol copolymer" means a polymer of vinyl alcohol/vinyl acetate with comonomers. Polyvinyl alcohol copolymers are also termed as "copolymer of polyvinyl alcohol" in this application.

It is known that polyvinyl alcohol is produced by hydrolysis (deacetylation) of polyvinyl acetate, whereby the ester groups of polyvinyl acetate are hydrolysed into hydroxyl groups, thus forming polyvinyl alcohol.

The degree of hydrolysis is a criteria of how many groups are converted into hydroxyl groups. The term "polyvinyl alcohol" in connection with a given degree of hydrolysis means therefore, in fact, a vinyl polymer containing ester and hydroxyl groups.

According to the invention polyvinyl alcohol copolymers with degrees of hydrolysis from 85 to 99.9%, especially between 85 to 95% are used.

The degree of hydrolysis of polyvinyl alcohol was determined according to DIN 53401.

The polyvinyl alcohol polymers according to the invention contain additional comonomers, i.e. other comonomers are polymerized together with vinylester in a first step (=copolymerization), followed by the hydrolysis of the ester groups to form the copolymer of polyvinyl alcohol in a second step.

It is state of the art to prepare copolymers of polyvinyl alcohol by a radical polymerization reaction between the vinyl acetate and comonomers.

According to the invention polyvinyl alcohol copolymers are preferred which were obtained by the copolymerization with a copolymerisable ethylenic unsaturated hydrocarbons as comonomers. These unsaturated hydrocarbons are optionally modified with functional non-charged and/or charged groups.

In particular one of the following comonomers are suitable:
  unsaturated hydrocarbons with 2 or 3 carbon atoms and no functional group, e.g. ethylene
  unsaturated hydrocarbons having 2 to 6 carbon atoms and non-charged functional groups like hydroxyl groups, e.g. 2,3-Buten-1,4 diol
  unsaturated hydrocarbons having anionic groups like carboxyl- and/or sulfonic acid groups.
  unsaturated hydrocarbons having cationic groups like quaternary ammonium salt groups It is preferred according to the invention to use polyvinyl alcohol copolymers with hydrolysis degrees from 85 to 99.9, preferred 85% to 95% and containing
  0.1 to 30 mol % comonomers with anionic groups or
  0.1 to 30 mol % comonomers with cationic groups like quaternary ammonium salt groups or
  0.1 to 30 mol % comonomers with unsaturated hydrocarbons having 2 to 6 carbon atoms and non-charged functional groups, especially two hydroxyl groups,
wherein mol % is based on polymerization mixture vinyl acetate/comonomer.

Suitable copolymers of polyvinyl alcohol and comonomers having a 1,2 diol structure, are described in EP 2426172 and EP 2648211 which disclosure is incorporated by reference hereby.

Examples for comonomers with anionic groups include acrylic acid, methacyrylic acid, itaconic acid, fumaric acid, maleic acid, maleic anhydride, 2-Acrylamido-2-methylpropane sulfonic acid, or other ethylenic unsaturated comonomers with carboxylate, phosphate or sulfonic groups.

The anionic group can be formed during the conditions of the copolymerization or afterwards by hydrolysis, e.g. alkaline or acidic hydrolyses of the obtained polyvinyl alcohol copolymers.

Following protective colloids are particular suitable for the production of microcapsules according to the invention:
  Anionic polyvinyl alcohol copolymers with the hydrolysis degree>80%—preferably 85.0%-99.5% and the viscosity 2 mPa*s-70 mPa*s (DP 100-6000). Examples of such colloids are: K-Polymer KL-318 from Kuraray (viscosity 20-30 mPa*s, hydrolysis 85.0-90.0%), Gohsenal T-350 from Nippon Gohsei (viscosity 27-33 mPa*s, hydrolysis 93.0-95.0%), Gohseran L-3266 from Nippon Gohsei (viscosity 2.3-2.7 mPa*s, hydrolysis 86.5-89.0%).

Non-charged polyvinyl alcohol copolymers with the hydrolysis degree>80%—preferably 85.0%-99.5% and the viscosity 2 mPa*s-70 mPa*s (DP 100-6000).

Examples of such type of colloids are: G-polymer OKS-8041 from Nippon Gohsei (viscosity 2.8-3.3 mPa*s, hydrolysis 88.0-90.0%), G-polymer AZF-8035 from Nippon Gohsei (viscosity 2.8-3.3 mPa*s, hydrolysis 98.5-99.5%)

Cationic polyvinyl alcohol copolymers with the hydrolysis degree>80%—preferably 85.0%-99.5% and the viscosity 2 mPa*s-70 mPa*s (DP 100-6000).

Example of such type of colloid is Gohsefimer K-210 from Nippon Gohsei (viscosity 18.0-22.0 mPa*s, hydrolysis 85.5-88.0%).

Preferred are copolymers of of polyvinyl alcohol with hydrolysis degrees from 85 to 99.9, preferred 85% to 95% and containing 0.1 to 30 mol % comonomers with anionic groups or 0.1 to 30 mol % comonomers with unsaturated hydrocarbons having 2 to 6 carbon atoms and two hydroxyl groups, wherein mol % is based on polymerization mixture vinyl acetate/comonomer.

In particular preferred are copolymers of polyvinyl alcohol with the above mentioned hydrolysis degrees from 85 to 99.9, preferred 85% to 95% and containing 0.1 to 15, especially 0.1 to 10 mol % comonomers with anionic groups or 0.1 to 15 mol % comonomers with unsaturated hydrocarbons having 2 to 6 carbon atoms and two hydroxyl groups.

Excellent results in leakage and stability of the capsules can be obtained, when copolymers of polyvinyl alcohol with the above mentioned hydrolysis degrees are used containing 0.1-30 mol %, especially 0.1 to 15 and in particular 0.1 to 10 mol % comonomers with sulfonic and/or carboxylat groups as anionic groups.

The protective colloid can be, but does not have to be, a constituent of the microcapsule shell.

In general, the protective colloids are used with amounts from 0.1 to at most 20% by weight, but preferably in the range from 1 to 10% by weight and in particular from 1.5 to 5% by weight, based on the weight of the capsules.

Combinations of two or more different protective colloids may also be beneficial.

Isocyanates

Isocyanates are N-substituted organic derivatives (R—N═C═O) of isocyanic acid (HNCO) tautomeric in the free state with cyanic acid. Organic isocyanates are compounds in which the isocyanate group (—N═C═O) is bonded to an organic radical. Polyfunctional isocyanates are those compounds with two or more isocyanate groups in the molecule.

According to the invention, at least bifunctional, preferably polyfunctional, isocyanates are used as (A), i.e. all aromatic, alicyclic and aliphatic isocyanates are suitable provided they have at least two reactive isocyanate groups.

The suitable polyfunctional isocyanates (A) preferably contain on average 2 to at most 4 NCO groups. Preference is given to using diisocyanates, i.e. esters of isocyanic acid with the general structure O═C═N—R—N═C═O, where R' here is aliphatic, alicyclic or aromatic radicals.

Suitable isocyanates (A) are, for example, 1,5-naphthylene diisocyanate, 4,4'-diphenylmethane diisocyanate (MOI), hydrogenated MDI (H12MDI), xylylene diisocyanate (XDI), tetramethylxylol diisocyanate (TMXDI), 4,4'-diphenyldimethylmethane diisocyanate, di- and tetraalkyldiphenylmethane diisocyanate, 4,4'-dibenzyl diisocyanate, 1,3-phenylene diisocyanate, 1,4-phenylene diisocyanate, the isomers of tolylene diisocyanate (TDI), optionally in a mixture, 1-methyl-2,4-diisocyanatocyclohexane, 1,6-diisocyanato-2,2,4-trimethylhexane, 1,6-diisocyanato-2,4,4-trimethylhexane, 1-isocyanatomethyl-3-isocyanato-1,5,5-trimethylcyclohexane, chlorinated and brominated diisocyanates, phosphorus-containing diisocyanates, 4,4'-diisocyanatophenylperfluoroethane, tetramethoxybutane 1,4-diisocyanate, butane 1,4-diisocyanate, hexane 1,6-diisocyanate (HDI), dicyclohexylmethane diisocyanate, cyclohexane 1,4-diisocyanate, ethylene diisocyanate, phthalic acid bisisocyanatoethyl ester, also polyisocyanates with reactive halogen atoms, such as 1-chloromethylphenyl 2,4-diisocyanate, 1-bromomethylphenyl 2,6-diisocyanate, 3,3-bischloromethyl ether 4,4'-diphenyldiisocyanate. Sulfur-containing polyisocyanates are obtained, for example, by reacting 2 mol of hexamethylene diisocyanate with 1 mol of thiodiglycol or dihydroxydihexyl sulfide. Further suitable diisocyanates are trimethylhexamethylene diisocyanate, 1,4-diisocyanatobutane, 1,2-diisocyanatododecane and dimer fatty acid diisocyanate.

Suitable isocyanates of type (A) are at least bifunctional compounds (i.e. compounds containing at least two isocyanate groups —N═C═O).

Typical representatives may be hexamethylene diisocyanate (HDI), or derivatives thereof, e.g. HDI biuret (commercially available e.g. as Desmodur N3200), HDI trimers (commercially available as Desmodur N3300) or else dicyclohexylmethane diisocyanates (commercially available as Desmodur W). Toluene 2,4-diisocyanate or diphenylmethane diisocyanate is likewise suitable.

Preferred according to the invention are isocyanates of type (A), selected from the group consisting of hexane 1,6-diisocyanate, hexane 1,6-diisocyanate biuret or oligomers of hexane 1,6-diisocyanate, in particular trimers thereof or dicyclohexanemethylene diisocyanate.

Preferably, the isocyanate (A) is an alicyclic or aliphatic isocyanate, wherein the alicyclic isocyanate is even more preferred.

One essential feature of the present process is the use of two structurally different isocyanates (A) and (B).

The second isocyanate of type (B) is structurally different from the isocyanate of type (A) and specifically the isocyanate of type (B) could either be an anionically modified isocyanate or a polyethylene oxide-containing isocyanate (or any desired mixtures of these two isocyanate types).

The anionically modified isocyanates are known per se. Preferably, these isocyanates of type (B) contain at least two isocyanate groups in the molecule. One or more sulfonic acid radicals are preferably present as anionic groups. Preferably, isocyanates of type (B) are selected which are oligomers, in particular trimers, of hexane 1,6-diisocyanate (HDI). Commercial products of these anionically modified isocyanates are known, for example, under the brand Bayhydur (Bayer), e.g. Bayhydur XP.

Polyethylene oxide-containing isocyanates (with at least two isocyanate groups) are also known and are described, e.g. in U.S. Pat. No. 5,342,556. Some of these isocyanates are self-emulsifying in water, which may be advantageous within the context of the present process since it may be possible to dispense with a separate emulsifying step.

The weight ratio of the two isocyanates (A) and (B) is adjusted preferably in the range from 10:1 to 1:10, more preferably in the range from 5:1 to 1:5 and in particular in the range from 3:1 to 1:1.

It is also possible to use mixtures of different isocyanates of types (A) and (B). Besides the isocyanates (A) and (B), further isocyanates can also additionally be used in the process according to the invention.

Preferably, however, a mixture of isocyanate (A) and an anionically modified isocyanate (B) is used, wherein the anionically modified diisocyanates (B) are selected from the group which contains at least one sulfonic acid group, preferably an aminosulfonic acid group, in the present process.

In general it is preferred to use 0.5-12 wt. % total sum of isocyanates (A) and (B) based on the total weight of the compounds used in the process.

Amines

At least bifunctional amines, but preferably polyethyleneimines (PEI), are used as further component in the process according to the invention. Polyethyleneimines are generally polymers in the main chains of which there are NH groups which are separated from one another in each case by two methylene groups:

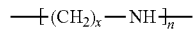

x = 2

Polyethyleneimines belong to the polyelectrolytes and the complexing polymers. Short-chain, linear polyethyleneimines with a correspondingly high fraction of primary amino groups, i.e. products of the general formula $H_2N\text{---}[CH_2\text{---}CH_2\text{---}NH\text{---}]_nH$ (n=2: diethylenetriamine; n=3; Methylenetetramine; n=4: tetraethylenepentamine) are sometimes called polyethyleneamines or polyalkylenepolyamines.

In the processes according to the invention, polyethyleneimines with a molecular weight of at least 500 g/mol, preferably from 600 to 30 000 or 650 to 25 000 g/mol and in particular from 700 to 5000 g/mol or 850 to 2500 g/mol, are preferably used. In general it is preferred to use 0.3-10 wt. %, in particular between 0.5-5 wt. %, polyethyleneimines based on the total weight of the compounds used in the process.

Though the process works with all water-insoluble liquid materials as mentioned above, according to the invention the microcapsules are "perfume free", i.e. the claimed microcapsules do not contain any fragrances or perfumes as water-insoluble liquid materials. Another object of the application are perfume-free microcapsules with a diameter from 1 to 30 μm comprising a liquid core of a water-insoluble liquid, and a shell of a reaction product of an at least bifunctional isocyanate (A) or a mixture of two or more different isocyanates containing (A) and an at least bifunctional amine in presence of polyvinyl alcohol copolymer with hydrolysis degrees above 85 to 99.9% as a protective colloid.

Water-Insoluble Liquid Material

The microcapsules produced using the process described above contain in the interior a material that is preferably water-insoluble and liquid at 21° C. (i.e. at 21° C., a maximum of 10 g of the material can be dissolved in 1 l of water). This includes all types of hydrophobic water-insoluble liquids, and any blends thereof. Excluded are any fragrances or perfumes as such materials.

The water-insoluble liquid material is also referred to herein below as "oil". These oils must be able, preferably without auxiliaries, to dissolve the isocyanates in order to be able to use them in the present process. Should an oil not ensure adequate solubility of the isocyanates, there is the option of overcoming this disadvantage by using suitable solubility promoters.

Besides the aforementioned oils, the microcapsules can also have further, optionally liquid or solid, ingredients which are dissolved, dispersed or emulsified in the oil in the microcapsules.

The phrase "oil" in the context of the present invention encompasses all kinds of oil bodies or oil components, in particular vegetable oils like e.g. rape seed oil, sunflower oil, soy oil, olive oil and the like, modified vegetable oils e.g. alkoxylated sunflower or soy oil, synthetic (tri)glycerides like e.g. technical mixtures of mono, di and triglycerides of C6-C22 fatty acids, fatty acid alkyl esters e.g. methyl or ethyl esters of vegetable oils (Agnique® ME 18 RD-F, Agnique® ME 18 SD-F, Agnique® ME 120-F, Agnique® ME1270, all products of Cognis GmbH, Germany) fatty acid alkyl esters based on said C6-C22 fatty acids, mineral oils and their mixtures. In one form the oil comprises preferably minerals oils.

Examples illustrating the nature of suitable hydrophobic carriers without limiting the invention to these examples are: Guerbet alcohols based on fatty alcohols having 6 to 18, preferably 8 to 10, carbon atoms, esters of linear C6-C22-fatty acids with linear or branched C6-C22-fatty alcohols or esters of branched C6-C 13-carboxylic acids with linear or branched C6-C 22-fatty alcohols, such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear C6-C22-fatty acids with branched alcohols, in particular 2-ethylhexanol, esters of C18-C38-alkylhydroxy carboxylic acids with linear or branched C6-C22-fatty alcohols, in particular Dioctyl Malate, esters of linear and/or branched fatty acids with polyhydric alcohols (such as, for example, propylene glycol, dimerdiol or trimertriol) and/or Guerbet alcohols, triglycerides based on C6-C10-fatty acids, liquid mono-/di-/triglyceride mixtures based on C6-C18-fatty acids, esters of C6-C22-fatty alcohols and/or Guerbet alcohols with aromatic carboxylic acids, in particular benzoic acid, esters of C2-C12-dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, linear and branched C6-C22-fatty alcohol carbonates, such as, for example, dicaprylyl carbonate (Cetiol® CC), Guerbet carbonates, based on fatty alcohols having 6 to 18, preferably 8 to 10, carbon atoms, esters of benzoic acid with linear and/or branched C6-C22-alcohols, linear or branched, symmetrical or asymmetrical dialkyl ethers having 6 to 22 carbon atoms per alkyl group, such as, for example, dicaprylyl ether, ring-opening products of epoxidized fatty acid esters with polyols, silicone oils (cyclomethicones, silicone methicone grades, etc.), aliphatic or naphthenic hydrocarbons, such as, for example, squalane, squalene or dialkylcyclohexanes, and/or mineral oils. In one form the oil comprises preferably aliphatic or naphthenic hydrocarbons and/or mineral oils.

Within the context of the present invention, preferred oils are, Guerbet alcohols based on fatty alcohols having 6 to 18, preferably 8 to 10, carbon atoms, esters of linear C6-C22-fatty acids with linear or branched C6-C22-fatty alcohols or esters of branched C6-C13-carboxylic acids with linear or branched C6-C22-fatty alcohols, such as e.g. myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate.

Also preferred oils are esters of linear C6-C22-fatty acids with branched alcohols, in particular 2-ethylhexanol, esters of C18-C38-alkylhydroxycarboxylic acids with linear or branched C6-C22-fatty alcohols, linear or branched C6-C22-fatty alcohols, in particular dioctyl malates, esters of linear and/or branched fatty acids with polyhydric alcohols (such as e.g. propylene glycol, dimerdiol or trimertriol) and/or Guerbet alcohols, triglycerides based on C6-C10-fatty acids, liquid mono-/di-/triglyceride mixtures based on C6-C18-fatty acids, esters of C6-C22-fatty alcohols and/or Guerbet alcohols with aromatic carboxylic acids, in particular benzoic acid, esters of C2-C12-dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, linear and branched C6-C22-fatty alcohol carbonates, such as e.g. dicaprylyl carbonate (Cetiol™ CC), Guerbet carbonates based on fatty alcohols having 6 to 18, preferably 8 to 10, carbon atoms, esters of benzoic acid with linear and/or branched C6-C22-alcohols (e.g. Finsolv™ TN), linear or branched, symmetrical or asymmetrical dialkyl ethers having 6 to 22 carbon atoms per alkyl group, such as e.g. dicaprylyl ether (Cetiol™ OE), ring-opening products of epoxidized fatty acid esters with polyols, silicone oils (cyclomethicones, silicon methicone types etc.) and/or aliphatic or naphthenic hydrocarbons, such as e.g. squalane, squalene or dialkylcyclohexanes.

Further suitable oils or oil constituents may be UV filter substances. Typical oil-soluble UV-B filters or broad-spectrum UV NB filters are, for example, 3-benzylidenecamphor or 3-benzylidenenorcamphor and derivatives thereof, e.g. 3-(4-methylbenzylidene)-camphor, 3-(4'-trimethylammonium)benzylidenebornan-2-one methylsulfate (Mexoryl® SO), 3,3'-(1,4-phenylenedimethine)bis(7,7-dimethyl-2-oxo-bicycle-[2.2.1]heptane-1-methanesulfonic acid) and salts (Mexoryl® SX), 3-(4'-sulfo)benzylidenebornan-2-one and salts (Mexoryl® SL), polymer of N-{(2 and 4)[2-oxoborn-3-ylidene)methyl}benzyl]acrylamide (Mexoryl® SW), 2-(2H-benzotriazol-2-yl)-4-methyl-6-(2-methyl-3-(1,3,3,3-tetramethyl-1-(trimethylsilyloxy)disiloxanyl)propyl)phenol (Mexoryl® SL), 4-aminobenzoic acid derivatives, preferably 2-ethylhexyl 4-(dimethylamino)benzoate, 2-octyl 4-(dimethylamino)benzoate and amyl 4-(dimethylamino)benzoate; esters of cinnamic acid, preferably 2-ethylhexyl 4-methoxycinnamate, propyl 4-methoxycinnamate, isoamyl 4-methoxycinnamate, 2-ethylhexyl 2-cyano-3,3-phenylcinnamate (octocrylene); esters of salicylic acid, preferably 2-ethylhexyl salicylate, 4-isopropylbenzyl salicylate, homomenthyl salicylate; derivatives of benzophenone, preferably 2-hydroxy-4-methoxybenzophenone, 2-hydroxy-4-methoxy-4'-methylbenzophenone, 2,2'-dihydroxy-4-methoxybenzophenone; esters of benzalmalonic acid, preferably di-2-ethylhexyl 4-methoxybenzmalonate; triazine derivatives, such as e.g. 2,4,6-trianilino(p-carbo-2'-ethyl-1-hexyloxy)-1,3,5-triazine and 2,4,6-tris[p-(2-ethylhexyloxy-carbonyl)anilino]-1,3,5-triazine (Uvinul® T 150) or bis(2-ethylhexyl) 4,4'-[(6-[4-((1,1-dimethylethyl)aminocarbonyl)phenylamino]-1,3,5-triazine-2,4-diyl)diimino]bisbenzoate (Uvasorb® HEB); 2,2-(methylenebis(6-(2H-benzotriazol-2-yl)-4-(1,1,3,3-tetramethylbutyl)phenol (Tinosorb® M); 2,4-bis[4-(2-ethylhexyloxy)-2-hydroxyphenyl]-6-(4-methoxyphenyl)-1,3,5-triazine (Tinosorb® S); propane-1,3-diones, such as e.g. 1-(4-tert-butylphenyl)-3-(4'-methoxyphenyl) propane-1,3-dione; ketotricyclo(5.2.1.0)decane derivatives, dimethicodiethyl benzalmalonate (Parsol® SLX).

Furthermore, liquid linear and/or branched and/or saturated or unsaturated hydrocarbons or any desired mixtures thereof can be used as oils within the context of the present invention. These may be e.g. alkanes having 4 to 22, preferably 6 to 18, carbon atoms, or any desired mixtures thereof. Also of suitability are the unsaturated hydrocarbons having 4 to 22 carbon atoms, or unsaturated hydrocarbons of identical carbon number, and any desired mixtures of these hydrocarbons. Cyclic hydrocarbons and aromatics, e.g. toluene and mixtures thereof may also be oils within the context of the present invention. In another form the oil comprises aromatics. Also suitable are silicone oils. Any desired mixtures of all of the specified core materials are also suitable.

It is also possible for other liquid, preferably water-insoluble materials, such as thickeners, silicone defoamers, oil soluble corrosion inhibitors and similar additives, like extreme pressure additives, yellow metal deactivators and the like, dyes or oil-soluble medicaments, emollients, odor absorbing compounds, cosmetic oil phases, film forming additive, pearlizer, vitamins, dyes to be used and be present in the microcapsules. Any desired mixtures of these further materials may also be present in the microcapsules. In cases where such material is not oil-soluble, additives may be used for dispersing or emulsifying it. Otherwise, many actives, as for example biocides or dyes often only available as blends with an oily solvent. Those compositions are also useful in the context of the present invention. Most preferred is the use of emollients, dyes, and UV-filters in the microcapsules of the present invention.

Emollients

The microcapsules could also contain emollients. An emollient is a material that softens, soothes, supplies, coats, lubricates, moisturizes, or cleanses the skin. An emollient typically accomplishes several of these objectives such as soothing, moisturizing, and lubricating the skin. Suitable emollients are mostly selected from the oils as described above. Emollients useful in the present invention can be petroleum-based, fatty acid ester type, alkyl ethoxylate type, fatty acid ester ethoxylates, fatty alcohol type, polysiloxane type, or mixtures of these emollients.

Dyes

The microcapsules may also contain dyes, preferably any dyes suitable and approved for cosmetic purposes. Examples include cochineal red A (C.I. 16255), patent blue V (C.I. 42051), indigotin (C.I. 73015), chlorophyllin (C.I. 75810), quinoline yellow (C.I. 47005), titanium dioxide (C.I. 77891), indanthrene blue RS (C.I. 69800) and madder lake (C.I. 58000). These dyes are normally used in concentrations of 0.001 to 0.1% by weight, based on the mixture as a whole.

Besides the before mentioned compounds the microcapsules of the present invention may also contain any desired blends of oils, as well as blends of oil and water in emulsified form. Any kind of emulsion (water-in-oil or oil-in-water, or multiple emulsions) is possible.

For this purpose emulsifiers are needed: The microcapsules according to the present invention might also contain one or more emulsifier. Suitable emulsifiers are, for example, nonionic surfactants from at least one of the following groups: products of the addition of 2 to 30 mol ethylene oxide and/or 0 to 5 mol propylene oxide onto linear $C_{6-22}$ fatty alcohols, onto $C_{12-22}$ fatty acids, onto alkyl phenols containing 8 to 15 carbon atoms in the alkyl group and onto alkylamines containing 8 to 22 carbon atoms in the alkyl group; alkyl oligoglycosides containing 8 to 22 carbon atoms in the alkyl group and ethoxylated analogs thereof; addition products of 1 to 15 mol ethylene oxide onto castor oil and/or hydrogenated castor oil; addition products of 15 to 60 mol ethylene oxide onto castor oil and/or hydrogenated castor oil; partial esters of glycerol and/or sorbitan with unsaturated, linear or saturated, branched fatty acids containing 12 to 22 carbon atoms and/or hydroxycarboxylic acids containing 3 to 18 carbon atoms and addition products thereof onto 1 to 30 mol ethylene oxide; partial esters of polyglycerol (average degree of self-condensation 2 to 8), polyethylene glycol (molecular weight 400 to 5,000), trimethylolpropane, pentaerythritol, sugar alcohols (for example sorbitol), alkyl glucosides (for example methyl glucoside, butyl glucoside, lauryl glucoside) and polyglucosides (for example cellulose) with saturated and/or unsaturated, linear or branched fatty acids containing 12 to 22 carbon atoms and/or hydroxycarboxylic acids containing 3 to 18 carbon atoms and addition products thereof onto 1 to 30 mol ethylene oxide; mixed esters of pentaerythritol, fatty acids, citric acid and fatty alcohol and/or mixed esters of fatty acids containing 6 to 22 carbon atoms, methyl glucose and polyols, preferably glycerol or polyglycerol, mono-, di- and trialkyl phosphates and mono-, di- and/or tri-PEG-alkyl phosphates and salts thereof, wool wax alcohols, polysiloxane/polyalkyl/polyether copolymers and corresponding derivatives, block copolymers, for example Polyethyleneglycol-30 Dipolyhydroxystearate; polymer emulsifiers, for example Pemulen types (TR-1, TR-2) of Goodrich; polyalkylene glycols and glycerol carbonate and ethylene oxide addition products.

It is likewise possible for the ingredients to migrate from the core of the microcapsules (i.e. the oil and/or further materials present in the core) into the shell.

The invention further provides aqueous dispersions comprising 5 to 50% by weight, based on the total weight of the dispersion, preferably from 15 to 40% by weight, of microcapsules which can be produced by the above process. A further preferred range is between 20 and 35% by weight. These aqueous dispersions are preferably obtained directly from the process described above.

The microcapsule dispersions which are obtained by the present process can be used in a large number of different applications, depending on the type of oil. Preference is given to using the microcapsules for the finishing of all kind of nonwovens, like wipes (for example wet wipes or dry wipes for cosmetic or cleaning purposes), but also for finishing papers (including wallpapers, toilet paper or papers for books and newsletters), for finishing diapers or sanitary napkins and similar hygienic products or textiles e.g. in order to finish the papers or textiles with a dye or an insecticide, or in cosmetic compositions, e.g. for producing sunscreen compositions which comprise the UV filter in the form of the microcapsules. Another use pertains to finishing diapers or sanitary napkins and similar hygienic products. Furthermore the microcapsules may be used in massage oils or crèmes or personal lubricants, and suppositories, e.g. to provide this products with anti-inflammatory actives.

Perfume-free microcapsules with a diameter from 1 to 30 μm containing a core of liquid water-insoluble material and a shell, prepared by (a) a premix (I) is prepared from water and a protective colloid;

(b) a further premix (II) is prepared from a water-insoluble liquid component and at least bifunctional isocyanate (A) or a mixture of two or more different isocyanates containing (A)

(c) the two premixes (I) and (II) are mixed together until an emulsion is formed and (d) at least a bifunctional amine is then poured into the emulsion from step (c) and (e) the emulsion is then heated up to at least 50° C. until the microcapsules are formed, characterized in that the protective colloid is a polyvinyl alcohol copolymer having hydrolysis degrees from 85 to 99.9%.

These microcapsules preferably have diameters from 1 to 30 μm and preferably diameters from 5 to 20 μm. They may be present in the form of an aqueous dispersion, where the fraction of the capsules can be 1 to 90% by weight, but preferably 5 to 50% by weight.

The present invention further relates to the use of the perfume-free microcapsules for finishing textiles, papers or nonwovens.

At least the present invention relates to the use of the perfume-free microcapsules in cosmetics, pharmaceutical, laundry and cleaning compositions.

The present invention has various advantages: The invention increases the stability of the microcapsules, especially the leakage and the stability of their dispersions.

EXAMPLES

Five microcapsule dispersions were produced using PVA with hydrolysis degree above 80% as protective colloids in the process according to the invention. For comparison, four microcapsule dispersions were prepared using different protective colloids or PVA with different hydrolysis degrees.

In each case the leakage evaluation of the capsules was determined and in some cases the capsule dispersion stability, viscosity or the particle size.

Particle Size Determination

The particle size determinations specified in the examples were carried out by means of static laser diffraction. The stated d 50 and d 90 values are based on the volume distribution of the particles.

Leakage Evaluation

For the leakage evaluation a known amount of capsule dispersion was stored for 3 days in 5 weight % sodium dodecyl sulfate solution (SDS) at 50° C. temperature. After this time the slurry was extracted 3 times with cyclohexane. Next, the solvent was evaporated and the residue was gravimetrically analysed.

Capsules Dispersion Stability Shelf-Life Evaluation

Capsule dispersion was stored at room temperature (20° C.) for 3 month in the graduated measuring glass. After this time the separation of dispersion was quantitatively measured.

Viscosity

Viscosity values of PVAs are the values of a 4 weight % aqueous solution determined at 20° C. by Brookfield viscometer.

I. Comparative Examples

Comparative Example 1 (with PVP Protective Colloid—not According to the Invention)

Microcapsules were prepared as follow:
A premix (I) was prepared from 50 g of PVP K90® (Polyvinylpyrrolidon with a K value about 90; BASF) and 1169 g of water and adjusted to a pH of 10.0 using aqueous sodium hydroxide solution (5% strength by weight). Premix II was prepared from 500 g of Myritol® 318 (caprylic/capric triglyceride from BASF), 58 g of Desmodur® W (dicyclohexylmethane diisocyanate from Bayer) and 39 g of Bayhydur® XP 2547 (anionic HDI oligomer from Bayer). These two premixes were combined and emulsified with the help of a MIG stirrer for 30 minutes at room temperature at a speed of 700 rpm. The pH of the emulsion was then adjusted to 8.5 using aqueous sodium hydroxide solution (5% strength by weight). Then, at room temperature and with stirring at 700 rpm, a solution of 37 g of Lupasol® PR8515 (Polyethyleneimine from BASF) in 147 g of water was added over the course of 1 minute. The reaction mixture was then subjected to the following temperature program: heating to 60° C. in 60 minutes, maintaining this temperature for 60 minutes, then 60 minutes at 70° C., 60 minutes at 80° C. and finally 60 minutes at 85° C. The mixture was then cooled to room temperature, giving the desired microcapsule dispersion with a fraction of nonvolatile components of 34% and a particle size distribution according to the following values: d 50=10 μm and d 90=21 μm.

Leakage of Myritol® 318 out of capsules: 52%

Capsules dispersion separation after 3 month (shelf-life stability): >40%

Comparative Example 2 (with PVA Protective Colloid—not According to the Invention)

Microcapsules were prepared as follow:
A premix (I) was prepared from 50 g of PVA (Mowiol® 8-88, Kuraray) and 1169 g of water and adjusted to a pH of 10.0 using aqueous sodium hydroxide solution (5% strength by weight). Premix II was prepared from 500 g of Myritol® 318 (caprylic/capric triglyceride from BASF) and 100 g of Desmodur® W (dicyclohexylmethane diisocyanate from Bayer). These two premixes were combined and emulsified with the help of a MIG stirrer for 30 minutes at room temperature at a speed of 700 rpm. The pH of the emulsion was then adjusted to 8.5 using aqueous sodium hydroxide solution (5% strength by weight). Then, at room temperature and with stirring at 700 rpm, a solution of 37 g of Lupasol® PR8515 (polyethyleneimine from BASF) in 147 g of water was added over the course of 1 minute. The reaction mixture was then subjected to the following temperature program: heating to 60° C. in 60 minutes, maintaining this temperature for 60 minutes, then 60 minutes at 70° C., 60 minutes at 80° C. and finally 60 minutes at 85° C. The mixture was then cooled to room temperature, giving the desired microcapsule dispersion with a fraction of nonvolatile components of 33% and a particle size distribution according to the following values: d 50=9 μm and d 90=16 μm.

Leakage of Myritol® 318 out of capsules: >60%

Capsules dispersion separation after 3 month (shelf-life stability): 15%

Comparative Example 3 (with PVA Protective Colloid—not According to the Invention)

Microcapsules were prepared as follow:
A premix (I) was prepared from 50 g of PVA (Mowiol® 8-88, Kuraray) and 1169 g of water and adjusted to a pH of 10.0 using aqueous sodium hydroxide solution (5% strength by weight).

Premix II was prepared from 500 g of Myritol® 318 (caprylic/capric triglyceride from BASF), 58 g of Desmodur® W (dicyclohexylmethane diisocyanate from Bayer) and 39 g of Bayhydur® XP 2547 (anionic HDI oligomer from Bayer). These two premixes were combined and emulsified with the help of a MIG stirrer for 30 minutes at room temperature at a speed of 700 rpm. The pH of the emulsion was then adjusted to 8.5 using aqueous sodium hydroxide solution (5% strength by weight). Then, at room temperature and with stirring at 700 rpm, a solution of 37 g of Lupasol® PR8515 (polyethyleneimine from BASF) in 147 g of water was added over the course of 1 minute. The reaction mixture was then subjected to the following temperature program: heating to 60° C. in 60 minutes, maintaining this temperature for 60 minutes, then 60 minutes at 70° C., 60 minutes at 80° C. and finally 60 minutes at 85° C. The mixture was then cooled to room temperature, giving the desired microcapsule dispersion with a fraction of nonvolatile components of 33% and a particle size distribution according to the following values: d 50=9 μm and d 90=17 μm.

Leakage of Myritol® 318 out of capsules: 64%

Capsules dispersion separation after 3 month (shelf-life stability): 10%

Comparative Example 4 (with Anionic PVA Protective Colloid Kuraray Poval 6-77 KL Mentioned in the WO 2012/107323 A1 Patent)

Microcapsules were prepared as follow:
A premix (I) was prepared from 50 g of anionic PVA (with hydrolysis degree 74%-80% and visc. 5.2-6.2 mPa*s, and carboxyl group content of 3 mol %) and 1169 g of water and adjusted to a pH of 10.0 using aqueous sodium hydroxide solution (5% strength by weight). Premix II was prepared from 500 g of Myritol® 318 (caprylic/capric triglyceride from BASF), 58 g of Desmodur® W (dicyclohexylmethane diisocyanate from Bayer) and 39 g of Bayhydur® XP 2547 (anionic HDI oligomer from Bayer). These two premixes were combined and emulsified with the help of a MIG stirrer for 30 minutes at room temperature at a speed of 700 rpm. The pH of the emulsion was then adjusted to 8.5 using aqueous sodium hydroxide solution (5% strength by weight). Then, at room temperature and with stirring at 700 rpm, a solution of 37 g of Lupasol® PR8515 (polyethyleneimine from BASF) in 147 g of water was added over the course of 1 minute. The reaction mixture was then subjected to the following temperature program: heating to 60° C. in 60 minutes, maintaining this temperature for 60 minutes, then 60 minutes at 70° C., 60 minutes at 80° C. and finally 60 minutes at 85° C. The mixture was then cooled to room temperature, giving the desired microcapsule dispersion with a fraction of nonvolatile components of 33% and a particle size distribution according to the following values: d 50=10 µm and d 90=17 µm.

Leakage of Myritol® 318 out of capsules: 58%
Capsules dispersion separation after 3 month (shelf-life stability): 10%

II. Examples According to This Invention

Example 5

Microcapsules were prepared as follows:
A premix (I) was prepared from 50 g of PVA-ethylene-copolymer (with hydrolysis degree 97.5-99.0% and visc. 23.0-30.0 mPa*s and ethane content of 2 mol %) and 1169 g of water and adjusted to a pH of 10.0 using aqueous sodium hydroxide solution (5% strength by weight). Premix II was prepared from 500 g of Myritol® 318 (caprylic/capric triglyceride) and 100 g of Desmodur0 W (dicyclohexylmethane diisocyanate). These two premixes were combined and emulsified with the help of a Mig stirrer for 30 minutes at room temperature at a speed of 700 rpm. The pH of the emulsion was then adjusted to 8.5 using aqueous sodium hydroxide solution (5% strength by weight). Then, at room temperature and with stirring at 700 rpm, a solution of 37 g of Lupasol® PR8515 (polyethyleneimine) in 147 g of water was added over the course of 1 minute. The reaction mixture was then subjected to the following temperature program: heating to 60° C. in 60 minutes, maintaining this temperature for 60 minutes, then 60 minutes at 70° C., 60 minutes at 80° C. and finally 60 minutes at 85° C. The mixture was then cooled to room temperature, giving the desired microcapsule dispersion with a fraction of nonvolatile components of 33% and a particle size distribution according to the following values: d 50=12 µm and d 90=20 µm.

Leakage of Myritol® 318 out of capsules: 56% Capsules dispersion separation after 3 month (shelf-life stability): 30%

Example 6

A premix (I) was prepared from 50 g of cationic modified PVA (with hydrolysis degree 85.5%-88.0% and visc. 18.0-22.0 mPa*s and ammonium group content of 2 mol %) and 1169 g of water. Premix II was prepared from 500 g of Myritol® 318 (caprylic/capric triglyceride from BASF), 58 g of Desmodur® W (dicyclohexylmethane diisocyanate from Bayer) and 39 g of Bayhydur® XP 2547 (anionic HDI oligomer from Bayer). These two premixes were combined and emulsified with the help of a MIG stirrer for 30 minutes at room temperature at a speed of 700 rpm. The pH of the emulsion was then adjusted to 8.5 using aqueous sodium hydroxide solution (5% strength by weight). Then, at room temperature and with stirring at 700 rpm, a solution of 37 g of Lupasol® PR8515 (polyethyleneimine from BASF) in 147 g of water was added over the course of 1 minute. The reaction mixture was then subjected to the following temperature program:

Heating to 60° C. in 60 minutes, maintaining this temperature for 60 minutes, then 60 minutes at 70° C., 60 minutes at 80° C. and finally 60 minutes at 85° C. The mixture was then cooled to room temperature, giving the desired microcapsule dispersion with a fraction of nonvolatile components of 32% and a particle size distribution according to the following values: d 50=9 µm and d 90=14 µm.

Leakage of Myritol® 318 out of capsules: 60%
Capsules dispersion separation after 3 month (shelf-life stability): 5%

Example 7

Microcapsules were prepared as follow:
A premix (I) was prepared from 50 g of carboxyl group-modified anionic PVA (with hydrolysis degree 85%-90%, visc. 20.0-30.0 mPa*s and carboxyl group content of 3 mol %) and 1169 g of water and adjusted to a pH of 10.0 using aqueous sodium hydroxide solution (5% strength by weight). Premix II was prepared from 500 g of Myritol® 318 (caprylic/capric triglyceride from BASF), 58 g of Desmodur® W (dicyclohexylmethane diisocyanate from Bayer) and 39 g of Bayhydur® XP 2547 (anionic HDI oligomer from Bayer). These two premixes were combined and emulsified with the help of a MIG stirrer for 30 minutes at room temperature at a speed of 700 rpm. The pH of the emulsion was then adjusted to 8.5 using aqueous sodium hydroxide solution (5% strength by weight). Then, at room temperature and with stirring at 700 rpm, a solution of 37 g of Lupasol® PR8515 (polyethyleneimine from BASF) in 147 g of water was added over the course of 1 minute. The reaction mixture was then subjected to the following temperature program: heating to 60° C. in 60 minutes, maintaining this temperature for 60 minutes, then 60 minutes at 70° C., 60 minutes at 80° C. and finally 60 minutes at 85° C. The mixture was then cooled to room temperature, giving the desired microcapsule dispersion with a fraction of nonvolatile components of 33% and a particle size distribution according to the following values: d 50=10 µm and d 90=17 µm.

Leakage of Myritol® 318 out of capsules: 41%
Capsules dispersion separation after 3 month (shelf-life stability): 10%

Example 8

A premix (I) was prepared from 50 g of sulfonic acid group modified anionic PVA (with hydrolysis degree 86.5%-89.5% and visc. 2.3-2.7 mPa*s and sulfonyl group content of 3 mol %) and 1169 g of water and adjusted to a pH of 10.0 using aqueous sodium hydroxide solution (5% strength by weight). Premix II was prepared from 500 g of Myritol® 318 (caprylic/capric triglyceride from BASF), 58 g of Desmodur® W (dicyclohexylmethane diisocyanate from Bayer) and 39 g of Bayhydur® XP 2547 (anionic HDI oligomer, from Bayer). These two premixes were combined and emulsified with the help of a MIG stirrer for 30 minutes at room temperature at a speed of 700 rpm. The pH of the emulsion was then adjusted to 8.5 using aqueous sodium hydroxide solution (5% strength by weight). Then, at room temperature and with stirring at 700 rpm, a solution of 37 g of Lupasol® PR8515 (polyethyleneimine from BASF) in 147 g of water was added over the course of 1 minute. The reaction mixture was then subjected to the following temperature program: heating to 60° C. in 60 minutes, maintaining this temperature for 60 minutes, then 60 minutes at 70° C., 60 minutes at 80° C. and finally 60 minutes at 85° C. The mixture was then cooled to room temperature, giving the desired microcapsule dispersion with a fraction of nonvolatile components of 32% and a particle size distribution according to the following values: d 50=12 μm and d 90=21 μm.

Leakage of Myritol® 318 out of capsules: 32%

Capsules dispersion separation after 3 month (shelf-life stability): 12%

Example 9

A premix (I) was prepared from 50 g of Butanediol/Vinyl Alcohol Copolymer (with hydrolysis degree 87%-90% and visc. 12.5-15.0 mPa*s, and butandiol content of 2 mol %) and 1169 g of water and adjusted to a pH of 10.0 using aqueous sodium hydroxide solution (5% strength by weight). Premix II was prepared from 500 g of Myritol® 318 (caprylic/capric triglyceride from BASF), 58 g of Desmodur® W (dicyclohexylmethane diisocyanate from Bayer) and 39 g of Bayhydur® XP 2547 (anionic HDI oligomer from Bayer). These two premixes were combined and emulsified with the help of a MIG stirrer for 30 minutes at room temperature at a speed of 700 rpm. The pH of the emulsion was then adjusted to 8.5 using aqueous sodium hydroxide solution (5% strength by weight). Then, at room temperature and with stirring at 700 rpm, a solution of 37 g of Lupasol® PR8515 (polyethyleneimine from BASF) in 147 g of water was added over the course of 1 minute. The reaction mixture was then subjected to the following temperature program: heating to 60° C. in 60 minutes, maintaining this temperature for 60 minutes, then 60 minutes at 70° C., 60 minutes at 80° C. and finally 60 minutes at 85° C. The mixture was then cooled to room temperature, giving the desired microcapsule dispersion with a fraction of nonvolatile components of 31% and a particle size distribution according to the following values: d 50=5 μm and d 90=11 μm.

Leakage of Myritol® 318 out of capsules: 46%

Capsules dispersion separation after 3 month (shelf-life stability): 3%

Example 10

A premix (I) was prepared from 50 g of carboxyl group-modified PVA (with hydrolysis degree 93%-95% and visc. 27.0-33.0 mPa*s and carboxyl group content of 4 mol %) and 1169 g of water. Premix II was prepared from 500 g of Myritol® 318 (caprylic/capric triglyceride from BASF), 58 g of Desmodur® W (dicyclohexylmethane diisocyanate from Bayer) and 39 g of Bayhydur® XP 2547 (anionic HDI oligomer from Bayer). These two premixes were combined and emulsified with the help of a MIG stirrer for 30 minutes at room temperature at a speed of 700 rpm. The pH of the emulsion was then adjusted to 8.5 using aqueous sodium hydroxide solution (5% strength by weight). Then, at room temperature and with stirring at 700 rpm, a solution of 37 g of Lupasol® PR8515 (polyethyleneimine from BASF) in 147 g of water was added over the course of 1 minute. The reaction mixture was then subjected to the following temperature program: heating to 60° C. in 60 minutes, maintaining this temperature for 60 minutes, then 60 minutes at 70° C., 60 minutes at 80° C. and finally 60 minutes at 85° C. The mixture was then cooled to room temperature, giving the desired microcapsule dispersion with a fraction of nonvolatile components of 33% and a particle size distribution according to the following values: d 50=9 μm and d 90=15 μm.

Leakage of Myritol® 318 out of capsules: 30%

Capsules dispersion separation after 3 month (shelf-life stability): 3%

Co-monomer amount within a polymer was determined using quantitative $^{13}$C and $^{1}$H NMR. In case of sulfur- or nitrogen-containing polymers elemental (C,H,N,S) analysis was performed in addition.

The invention claimed is:

1. A process for producing microcapsules which contain a shell and a core of a liquid water-insoluble material, comprising
    (a) preparing a premix (I) from water and a protective colloid;
    (b) preparing a further premix (II) from a water-insoluble liquid component and at least one bifunctional isocyanate (A) or a mixture of two or more different isocyanates containing (A) and an anionically modified diisocyanate (B) is used, wherein the anionically modified diisocyanates (B) are selected from the group which contain at least one sulfonic acid group in the molecule;
    (c) mixing the two premixes (I) and (II) together until an emulsion is formed; and
    (d) then pouring at least a bifunctional amine into the emulsion from step (c); and
    (e) then heating the emulsion to at least 50° C. until the microcapsules are formed,
    wherein the protective colloid is a polyvinyl alcohol copolymer having hydrolysis degrees from 85 to 99.9%; and
    wherein the polyvinyl alcohol copolymer contains 0.1 to 30 mol % comonomers with anionic groups.

2. The process as claimed in claim 1, wherein the polyvinyl alcohol copolymer has hydrolysis degrees between 85 to 95%.

3. The process as claimed in claim 1, wherein the polyvinyl alcohol copolymer contains 0.1-30 mol % comonomers with sulfonic and/or carboxylate groups as anionic groups.

4. The process as claimed in claim 1, wherein the at least one bifunctional isocyanate (A) is selected from the group consisting of hexane 1,6 diisocyanate, hexane 1,6 diisocyanate biuret, oligomers of hexane 1,6 diisocyanate, and dicyclohexanemethylene diisocyanate.

5. The process as claimed in claim 1, wherein the weight ratio between the isocyanates (A) and (B) is in the range from 10:1 to 1:10.

6. The process as claimed in claim 1, wherein the at least one bifunctional amine used is a polyethyleneimine.

7. The process as claimed in claim 1, wherein the core-shell ratio (w/w) of the microcapsules is 20:1 to 1:10.

8. The process as claim in claim 3 wherein the polyvinyl alcohol contains 0.1 to 15 mol % comonomers with sulfonic and/or carboxylate groups as anionic groups.

9. The process as claim in claim 8 wherein the polyvinyl alcohol contains 0.1 to 10 mol % comonomers with sulfonic and/or carboxylate groups as anionic groups.

10. The process as claimed in claim 4 wherein the at least one bifunctional isocyanate (A) comprises a trimer of hexane 1,6 diisocyanate or dicyclohexanemethylene diisocyanate.

* * * * *